United States Patent [19]

Leppert

[11] Patent Number: 4,885,001
[45] Date of Patent: Dec. 5, 1989

[54] PUMP WITH PLURAL FLOW LINES

[75] Inventor: Lawrence L. Leppert, Littleton, Colo.

[73] Assignee: Cobe Laboratories, Inc., Lakewood, Colo.

[21] Appl. No.: 202,106

[22] Filed: Jun. 3, 1988

[51] Int. Cl.⁴ .................................................. A61M 1/03
[52] U.S. Cl. .......................................... 604/4; 604/118; 128/DIG. 13
[58] Field of Search ........................................ 604/4–6, 604/43, 44, 118; 128/DIG. 13; 417/442; 210/646; 222/136, 244

[56] References Cited

U.S. PATENT DOCUMENTS 4,614,590  9/1986  Rath et al. ............................... 604/5
4,643,714  2/1987  Brose ....................................... 604/4

*Primary Examiner*—Stephen C. Pellegrino

[57] ABSTRACT

Apparatus for pumping fluid through plural flow lines comprising a pump having an inlet and an outlet for transporting the fluid therethrough, first and second flow lines that are selectively connectable to the pump inlet via a first valve, and third and fourth flow lines that are selectively connectable to the outlet via a second valve, whereby the pump can be used to selectively pump fluid through different flow paths.

21 Claims, 2 Drawing Sheets

PUMP WITH PLURAL FLOW LINES

FIELD OF THE INVENTION

The present invention relates to pumping fluid through plural flow lines, e.g., arterial and venous lines used in single needle dialysis.

BACKGROUND OF THE INVENTION

Single venipuncture needles have been used to cyclically remove untreated blood from a patient and return treated blood to a patient, e.g., in conjunction with fluid flow transfer devices such as dialyzers connected to the needles via arterial and venous flow lines and drip chambers.

One or two pumps can be used, and the pumps and valves on the flow lines are controlled so as to provide flow of untreated blood from the patient and into the arterial line during an arterial phase and flow of treated blood through the venous line to the patient during a venous phase, e.g. as is described in Brose U.S. Pat. No. 4,643,14. If two pumps are used, they are generally alternately operated so that only one is on at one time. If one pump is used, it is operated continuously, and the pressures vary widely during the arterial and venous phases.

SUMMARY OF THE INVENTION

It has been discovered that fluid pumping could be efficiently provided by a single pump in a system having plural flow lines by making first and second lines selectively connectable to the pump inlet by a first valve and third and fourth lines selectively connectable to the pump outlet by a second valve. The pump can thus be used at different times to pump fluid through different flow paths, eq., through a path including the first and third lines or a path including the second and fourth lines.

In preferred embodiments the pump is a peristaltic pump having a pump header; the fluid flow system in which the system is used is a single needle dialysis system; the system utilizes expansion chambers and drip chambers; and the system has various phases including a draw phase in which blood is drawn from the patient through the first line and pumped through the fourth line to the dialyzer, a first transitional phase in which the untreated blood in the pump header is pumped into the fourth line and replaced by treated blood from the dialyzer through the second line, a return phase in which treated blood is pumped from the dialyzer through the second line and returned through the third line to the patient, and a second transitional phase in which treated blood in the pump header is pumped into the third line and is replaced by untreated blood from the first line. The first transitional phase avoids returning untreated blood in the header to the patient at the beginning of the return phase. The second transitional phase avoids processing blood twice, promoting efficiency. The present invention has advantage over some present single-pump systems in avoiding large pressure swings and has advantage over some present double-pump systems in continuous pump operation, promoting pump motor life.

Other advantages and features of the invention will be apparent from the following description of a preferred embodiment thereof and from the claims.

DESCRIPTION OF THE PREFERRED EMBODIMENT

We first briefly describe the drawings.

DRAWINGS

STRUCTURE

Figure 1:
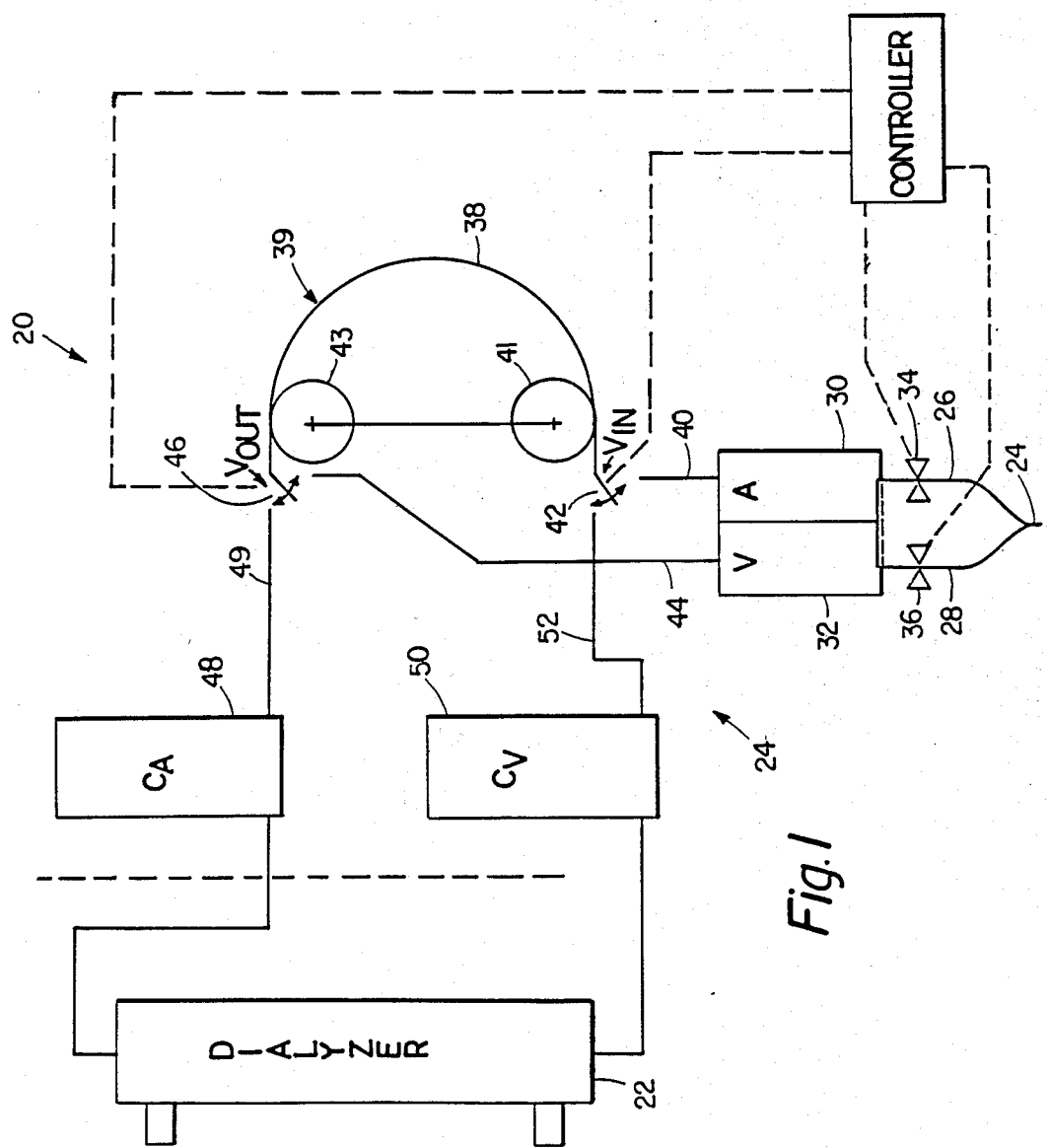
FIG. 1 is a diagrammatic representation of a pumping system according to the invention.

Referring to FIG. 1, there is shown single needle dialysis apparatus 20 by removing untreated blood from a patient (not shown), treating the blood in hollow fiber dialyzer 22 ("fluid flow transfer device") and returning the blood to the patient. Apparatus 20 is connected to the patient via needle 24 and arterial and venous lines 26, 28. Arterial and venous lines 26, 28 are connected to patient arterial and venous drip chambers 30, 32 and controlled with pinch valves 34, 36.

Figure 2:
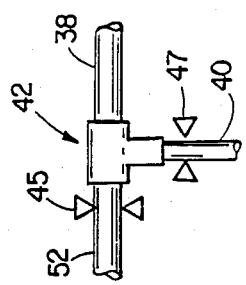
FIG. 2 is a diagram of a clamp valve used in the FIG. 1 system.

Arterial drip chamber 30 is connected to the inlet end of pump header 38 of peristaltic pump 39 via flow line 40 and clamp valve 42 (the "first valve"). Pump 39 has rollers 41, 43, which compress header 38. The structure of valve 42 is shown in FIG. 2; it includes two pinch clamps 45, 47 that are alternately opened and closed so that only one of line 40 (comprising with line 26 the "first line ") or line 52 is connected to the inlet of pump header 38 at once. Venous drip chamber 32 is connected to the outlet end of pump header 38 via flow line 44 (comprising with line 28 the "third line "), and clamp valve 46 (the "second valve "), having the same structure as clamp valve 42. The inlet of arterial expansion chamber 48 is connected via fluid line 49 (the "fourth line") to clamp valve 46. The outlet of arterial expansion chamber 48 is connected to dialyzer 22. The outlet of dialyzer 22 is connected to venous expansion chamber 50. The outlet of expansion chamber 50 is connected via fluid line 52 to clamp valve 42. Controller 60 is electrically connected to control valves 34, 36, 42, 46. Pinch valves 34, 36 are referred to as "fifth and sixth pinch valves". The pinch valves that are used are actuated by solenoids and returned by springs.

OPERATION

Figure 3A:
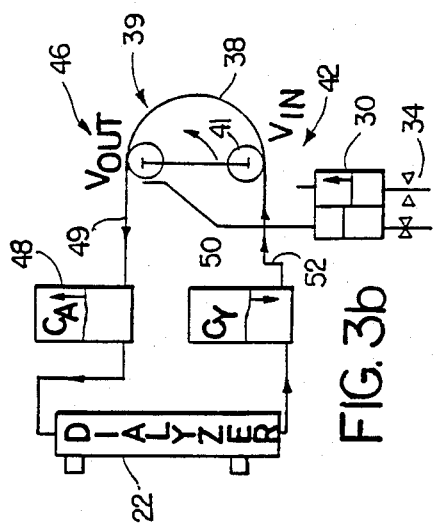
FIGS. 3A–3D are diagrammatic representations showing the flow paths of the FIG. 1 system during different phases.
Figure 3B:
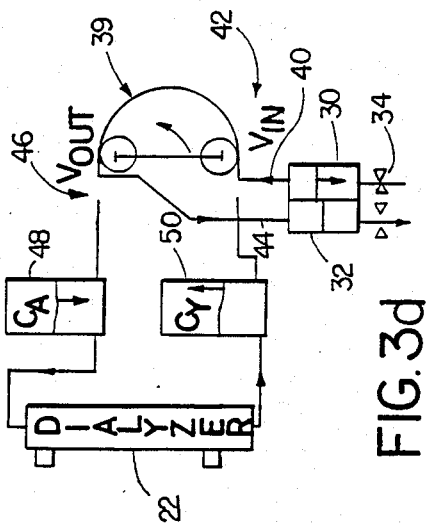
Figure 3C:
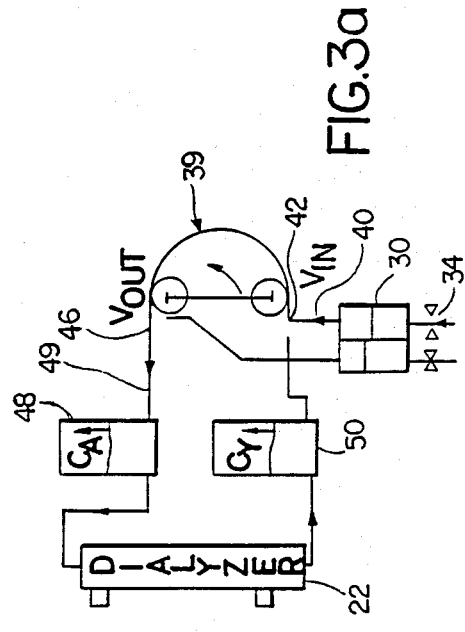
Figure 3D:
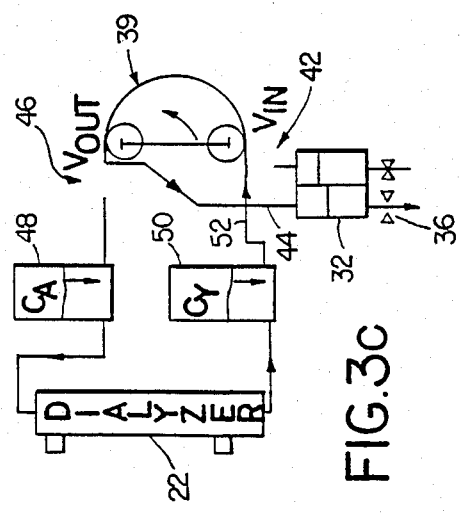

In operation, single needle apparatus 20 is repeatedly operated through four functional phases: the draw phase (FIG. 3A), the first transitional phase (FIG. 3B), the return phase (FIG. 3C), and the second transitional phase (FIG. 3D). Throughout these phases, clamp valves 42, 46 alternately clamp one of the two lines that they each respectively connect to pump header 38, thereby providing flow through the other flow line to or from pump header 38. E.g., clamp valve 42 alternately clamps line 40 with pinch clamp 47 and line 52 with pinch clamp 45.

Referring to FIG. 3a, in the draw phase, pump 39 is connected to line 40 via valve 42 and to line 49 via valve 46, and pinch valve 34 is opened to allow unprocessed blood to flow from the patient and into the hydraulic circuit, including flow of some of the blood through dialyzer 22, where it is treated. During this phase, the volumes in expansion chambers 48, 50 increase, and pressure downstream of pump 39 increases.

Referring to FIG. 3B, in the first transitional phase, which lasts for one-half revolution of pump 39, clamp valves 42, 46 connect pump header 38 to lines 52, 49, respectively. Unprocessed blood is moved from pump header 38 to expansion chamber 48 while processed blood from chamber 50 enters header 38. In addition, pinch valve 34 remains open to allow pressure in drip chamber 30 to stabilize, increasing the volume of unprocessed blood in chamber 30. The first transitional phase avoids returning the untreated blood that is within the pump header to the patient in the beginning of the return phase.

Referring to FIG. 3C, in the return phase, pump 39 is connected to lines 44, 52, and pinch valve 36 is opened. Treated blood is pumped from dialyzer 22 and returned to the patient. During this phase, the volumes of expansion chambers 48, 50 decrease, as do the pressures in them. Because blood can be returned to a patient faster than it can be removed from a patient, pump 39 may be operated faster in the return phase than in the draw phase, thereby speeding up flow of blood through the system.

Referring to FIG. 3D, in the second transitional phase, clamp valves 42, 46 connect pump 39 to lines 40, 44, and the processed blood in header 38 is replaced with unprocessed blood from chamber 30. The processed blood is returned to the patient, and the volume of blood in chamber 30 is decreased. The second transitional phase avoids treating blood in the dialyzer twice, thereby improving efficiency.

Because the present invention utilizes a single pump instead of two pumps, it maybe operated continuously; i.e. the pump motor does not have to be started and stopped (as with at least some two-pump designs), thus prolonging the useful life of the pump motor. The use of one pump also saves the expense of providing more than one pump per fluid flow apparatus. The present invention improves over some existing single-pump systems, because the invention has reduced pressure changes, and higher flowrates can be achieved at larger stroke volumes. Also, in the present invention the pump can be easily operated at different speeds in different phases, permitting one to take advantage of the fact that it is possible to return blood to a patient faster than the blood is drawn from the patient.

OTHER EMBODIMENTS

Other embodiments of the invention are within the scope of the following claims. E.g., arterial and venous lines 26, 28 may be connected directly to valves 42 and 46, respectively, and the second transitional phase can be omitted. Thus the processed blood which is in pump header 38 at the end of the return phase is processed by dialyzer 22 a second time.

What is claimed is:

1. Apparatus for pumping fluid through plural flow lines comprising
   a pump having an inlet and an outlet for transporting said fluid therethrough,
   first and second flow lines that are selectively connectable to said pump inlet via a first valve, and
   third and fourth flow lines that are selectively connectable to said outlet via a second valve,
   said first and third lines being inflow and outflow lines, respectively,
   said second and fourth lines being connected to a fluid flow transfer device,
   whereby said pump can be used to selectively pump fluid through different flow paths.

2. The apparatus of claim 1 wherein said pump is a peristaltic pump having a roller which compresses a header containing said fluid to move said fluid through said header, said header having said inlet and said outlet.

3. The apparatus of claim 1 wherein said fluid that is pumped through said plurality of flow lines is blood.

4. The apparatus of claim 1 wherein said first valve comprises, a first pinch valve connected to stop the flow of fluid through said first flow line and a second pinch valve connected to stop the flow of fluid through said second flow line, and
   wherein said second valve comprises a third pinch valve connected to stop the flow of fluid through said third flow line and a fourth pinch valve connected to stop the flow of fluid through said fourth flow line.

5. The apparatus of claim 1 further comprising
   a controller electrically connected to said first and second valves, wherein said controller controls said first valve to connect one of said first and second flow lines to said pump inlet at one time and controls said second valve to connect one of said third and fourth flow lines to said pump outlet at one time.

6. Apparatus for pumping fluid through plural flow lines, said apparatus being a single needle dialysis system, comprising
   a pump having an inlet and an outlet for transporting said fluid therethrough,
   first and second flow lines that are selectively connectable to said pump inlet via a first valve,
   third and fourth flow lines that are selectively connectable to said outlet via a second valve,
   a needle connected to said first and said third flow lines, and
   a dialyzer connected to said second and fourth flow lines,
   whereby said pump can be used to selectively pump fluid through different flow paths.

7. The apparatus of claim 6 further comprising
   a first expansion chamber connected along said fourth flow line between said second valve and said dialyzer, and
   a second expansion chamber connected along said second flow line between said first valve and said dialyzer.

8. The apparatus of claim 7 further comprising
   a first drip chamber connected along said first flow line and
   a second drip chamber connected along second flow line.

9. The apparatus of claim 8 further comprising
   fifth and sixth pinch valves connected to stop the flow of fluid through said first and third flow lines, respectively.

10. A method of pumping fluid through plural flow lines comprising
    providing a pump having an inlet and an outlet for transporting fluid therethrough, first and second flow lines that are selectively connectable to said pump inlet via a first valve, and third and fourth flow lines that are selectively connectable to said outlet via a second valve, said first and third lines being inflow and outflow lines, respectively, said second and fourth lines being connected to a fluid flow transfer device, switching said first valve to connect one of said first and second flow lines to said inlet and to disconnect the other, switching said second valve to connect one of said third and fourth flow lines to said outlet and to disconnect the other, and pumping fluid through said pump.

11. The method of claim 10 wherein said pumping is continuous, and said switching said first valve and said switching said second valve result in a plurality of phases with different flow paths through said first, second, third, and fourth flow lines.

12. A method of pumping fluid through plural flow lines comprising providing a pump having an inlet and an outlet for transporting fluid therethrough, first and second flow lines that are selectively connectable to said pump inlet via a first valve, and third and fourth flow lines that are selectively connectable to said outlet via a second valve, switching said first valve to connect one of said first and second flow lines to said inlet and to disconnect the other, switching said second valve to connect one of said third and fourth flow lines to said outlet and to disconnect the other, and pumping fluid through said pump, wherein said first and third lines are connected to remove blood from and return blood to a patient, said second and fourth lines are connected to a fluid flow transfer device, and one of said plurality of phases is a draw phase in which said first line is connected to said inlet, said fourth line is connected to said outlet, and untreated blood is pumped from said first line to said fourth line, thereby drawing blood from a patient.

13. The method of claim 12 wherein one of said phases is a return phase in which said second line is connected to said inlet, said third line is connected to said outlet, and treated blood is pumped from said second line to said third line, thereby returning treated blood to a patient.

14. The method of claim 13 wherein one of said phases is a first transitional phase in which said second line is connected to said inlet, said fourth line is connected to said outlet, and untreated blood in said pump is pumped to said fourth line and replaced by treated blood in said second line.

15. The method of claim 14 further comprising providing first and second drip chambers along said first and third flow lines, and wherein one of said phases is a second transitional phase in which said first flow line is connected to said inlet, said third flow line is connected to said outlet, and treated blood in said pump is pumped to said third line and replaced by untreated blood in said first line from said first drip chamber.

16. The method of claim 14 further comprising providing a first expansion chamber connected along said fourth flow line, and a second expansion chamber connected along said second flow line.

17. The method of claim 16 wherein said draw phase comprises increasing the volume in said first expansion chamber and said second expansion chamber.

18. The method of claim 17 wherein said return phase comprises decreasing the volume in said first expansion chamber and said second expansion chamber.

19. The method of claim 18 wherein said first transitional phase comprises filling said first expansion chamber and emptying said second expansion chamber.

20. The method of claim 19 further comprising providing first and second drip chambers along said first and third flow lines, and wherein one of said phases is a second transitional phase in which said first flow line is connected to said inlet, said third flow line is connected to said outlet, and treated blood in said pump is pumped to said third line and replaced by untreated blood in said first line from said first drip chamber.

21. The method of claim 20 wherein said second transitional phase comprises emptying said first expansion chamber and filling said second expansion chamber.

* * * * *